United States Patent [19]

Scaffidi

[11] Patent Number: 5,079,003
[45] Date of Patent: Jan. 7, 1992

[54] SKIN LOTIONS AND CREAMS

[76] Inventor: Adelia Scaffidi, 11432 W. 130th St., Strongsville, Ohio 44136

[21] Appl. No.: 493,194

[22] Filed: Mar. 14, 1990

[51] Int. Cl.$^5$ .......................... A61K 7/40; A61K 7/48
[52] U.S. Cl. .................................... 424/401; 424/523; 424/485; 514/847; 514/938
[58] Field of Search .................... 424/401, 485, 59; 514/844, 845, 846, 847, 937, 938, 943

[56] References Cited

U.S. PATENT DOCUMENTS

| | | | |
|---|---|---|---|
| 3,930,000 | 12/1975 | Margraf | 424/245 |
| 4,021,572 | 5/1977 | Van Scott et al. | 424/317 |
| 4,124,720 | 11/1978 | Wenmaekers | 424/278 |
| 4,189,465 | 2/1980 | Rosenthal | 424/10 |
| 4,216,201 | 8/1980 | Calvo | 424/63 |
| 4,454,159 | 5/1984 | Lay et al. | 424/81 |
| 4,454,159 | 6/1984 | Musher | 424/358 |
| 4,515,784 | 5/1985 | Bogardus et al. | 514/63 |
| 4,536,399 | 8/1985 | Flynn et al. | 514/63 |
| 4,595,586 | 6/1986 | Flom | 424/59 |
| 4,735,742 | 4/1988 | Ansmann | 514/943 |
| 4,737,360 | 4/1988 | Allen et al. | 514/938 |
| 4,760,096 | 7/1988 | Sakai et al. | 514/937 |
| 4,797,272 | 1/1989 | Linn et al. | 424/59 |
| 4,816,271 | 3/1989 | Scaffidi | 424/60 |

OTHER PUBLICATIONS

Data sheets from Croda, Inc. concerning Crodamol PTC, Super Steron Ester, and Polawax, CTFA, p. 420.
STN International Search Reports, Ca File.
Federal Register, vol. 43, No. 151: FDA, Skin Protectant Drug Products for Over-the Counter Use, excerpts.
Navvare, The Chemistry and Manufacture of Cosmetics, pp. 121-136.
Encyclopedia of Chemical Technology, Third Edition, Kirk-Othmer, pp. 147-150.

*Primary Examiner*—Thurman K. Page
*Assistant Examiner*—Edward J. Webman

[57] ABSTRACT

Cosmetic creams or lotions comprising emulsions of shark liver oil, squalane, and squalene along with numerous other ingredients with therapeutic and synergetic effects on the skin are disclosed.

3 Claims, No Drawings

SKIN LOTIONS AND CREAMS

INTRODUCTION

This invention relates to preparations for application to the skin. More particularly, it relates to lotions and creams incorporating fish oils, such as shark liver oil, squalane, and squalene, that are used as moisturizers, as bases for cosmetics, as hand and body lotions, and as sunburn preventives.

BACKGROUND AND SUMMARY OF THE INVENTION

Various compositions have been developed for the purpose of moisturizing the skin and protecting it from harsh detergents. The composition of such products may contain various ingredients in various proportions and percents that may alter or promote the synergetic effects of fish oils. The present invention is based upon the results of a series of research and experiments of an oil-in-water base emulsion that has synergetic ingredients that achieve and utilize the benefits of shark oils (i.e. shark liver oil, squalene, or squalane) and maintain a suitable shelf life, measured in years. A two-year shelf life has been found to be satisfactory.

Shark liver oil is an unsaturated oil that contains triglycerides, lipids, and fatty acids, and is especially noted for its high content of vitamin A and squalene, the latter being a highly unsaturated terpenic hydrocarbon that is a biochemical precursor of cholesterol. Squalene, in fact, is a constituent of normal skin sebum. A study of the prior art has revealed patents relating to shark liver oil, squalane, and squalene as constituents in cosmetic formulations. Examples of such prior art are: U.S. Pat. No. 4,189,465, issued to Rosenthal; U.S. Pat. No. 3,930,000, issued to Margraff; and U.S. Pat. No. 4,021,572, issued to Van Scott, et al—none of which have any pertenence with respect to the present invention. The present invention will show a method of preparation and ingredients that will not alter, but will promote the effects of fish oils with synergetic ingredients and maintain a stable emulsion.

DETAILED DESCRIPTION OF THE INVENTION

Many ingredients were investigated to determine their compatibility with shark liver oil emulsions. The invention will show a method of preparation and ingredients to be used to promote the beneficial effects of shark liver oil.

Antioxidants and preservatives must be used to protect shark oil against harmful microorganisms. Thus, preservatives such as diazolidinyl urea at a concentration of from 0.05 to 1.0 wt. % is needed. As an alternative, a mixture of BHT and BHA, each at 0.05 wt. % is highly to be desired. All three preservatives could be included in the formulation without detriment.

An emulsifier is needed to initially create a stable emulsion and a stabilizer is needed to maintain such an emulsion. Emulsifying wax as, for example the variety, "polawax" N.F. at 0.5 to 8.0 wt. %, stearic acid at 0.5 to 4.0 wt. %, glyceryl stearate at 0.5 to 5.0 wt. %, and cetyl alcohol at 0.5 to 2.0 wt. % are essential for shark oil to form a lotion or cream emulsion. Triethanolamine (TEA) at 0.02 to 1.0 wt. % is also essential to prevent separating of the emulsion, once it is formed.

There are many oils that can be combined with shark liver oil—oils such as sesame oil at up to 30 wt. %, almond oil at up to 30 wt. %, or lanolin at up to 3.0 wt. %; these oils appear to be the most superior, although most organic oils can be used. Squalane or squalene may be substituted for shark liver or used in combination with shark liver oil in a range of 0.5 to 30 weight percent.

Thickening agents such as xanthan gum at 0.2 to 0.5 wt. % or Carbopol at 0 to 0.2 wt. % are useful to help form an emulsion. Sodium salts, such as a sodium salt of ethylene diamine tetraacetic acid (EDTA) at 0 to 0.2 wt. %, are also helpful.

There are many esters used in cosmetic preparations. I have found PPG2 myristyl ether propionate promotes a synergetic effect with shark oils at 0.5 to 2.0 wt. %; pentaerythritol tetracaprate/caprylate (trade name "Crodamol P.T.C."), has a similar effect at 0.5 to 2.0 wt. %, as does $C_{12}$–$C_{15}$ alcohol benzoate at concentrations below 1 wt. %.

Many cholesterols are used in cosmetic formulations. I have found that $C_{10}$–$C_{30}$ carboxylic acid esters of sterols, predominantly the sterols cholesterol and lanosterol, may be used as an emollient and resemble the active part of sebum that has emulsion stabilizing properties. They also act as viscosity builders and have the ability to absorb up to 50% of its weight of water, which feature promotes the effect of shark liver oil. I prefer to use $C_{10}$–$C_{30}$ Cholesterol/Lanosterol Ester, trade name "Super Sterol Ester", at a concentration in the range of 0.1 to 8 wt. %.

When a fatty acid, such as stearic acid is used, it is essential to reduce or eliminate sudsing of the emulsion by using a defoaming agent, such as dimethicone at 0.1 to 4.0 wt. %. When fatty acids are absent, no defoaming agent is needed, although its inclusion does no harm.

If the shark liver oil has been refined, as by chromatography, thereby removing the naturally present vitamin A, then that vitamin may be replenished by adding retinyl palmitate $AD_3$ at 0.1 to 4.0 wt. %. This palmitate may also be used with squalane or squalene.

A humectant such as propylene glycol at 0.5–4.0 wt. %, or glycerine as an alternative at similar concentrations, is also desirable and is compatible with shark oils.

Other ingredients, such as collagen amino acids, hydrolyzed animal proteins, reticulin, and hydrolyzed elastin may be used. All of these materials are naturally synthesized by the human body and they are very compatible with shark liver oil, squalane, and squalene. I have found that each of these ingredients may be used in the range of 0 to 1.0 wt. % in a stable emulsion. Fragrance may be added as desired in a range of 0 tp 0.5%.

PREFERRED EMBODIMENT

The following examples are detailed descriptions of the preparation of two preferred embodiments of the present invention. The ingredient names are those commonly used by the Cosmetic Toiletry and Fragrance Association.

EXAMPLE 1

| Ingredient | Weight Percent |
| --- | --- |
| PHASE A: | |
| Water | as required for 100% |
| Xanthan gum | 0.2 |
| Carbopol | 0.02 |
| PHASE B: | |
| Propylene glycol | 4.0 |

| Ingredient | Weight Percent |
| --- | --- |
| Triethanolamine (TEA) | 0.5 |
| Tetrasodium EDTA | 0.05 |
| PHASE C: | |
| Squalane | 2.0 |
| Sesame oil | 2.0 |
| Shark liver oil | 0.5 |
| Lanolin | 0.5 |
| Emulsifying wax (pola wax) N.F. | 2.0 |
| PPG2 Myristyl ether propionate | 2.0 |
| Glyceral stearate | 1.0 |
| Dimethicone | 0.5 |
| Cetyl alcohol | 0.5 |
| Pentaerythritol tetra-caprate/caprylate | 1.0 |
| BHT | 0.05 |
| BHA | 0.05 |
| Stearic acid | 0.5 |
| Diazolidinyl urea | 1.0 |
| Fragrance | 0.5 | wherein, in making said composition, said water is first heated to 75 degrees Celsius and then the additional PHASE A ingredients are mixed in; PHASE B ingredients are added to PHASE A the resulting phase is mixed; PHASE C ingredients are mixed in a separate vessel at 75 degrees Celsius and then mixed into the combined PHASE A AND B. At 40 degrees Celsius, fragrance is added. The mixture has formed a stable emulsion.

EXAMPLE 2

| Ingredient | Weight Percent |
| --- | --- |
| PHASE A: | |
| Water | as required for 100% |
| Xanthan gum | 0.5 |
| Carbopol | 0.2 |
| PHASE B: | |
| Propylene glycol | 3.0 |
| Triethanolamine (TEA) | 0.5 |
| Tetrasodium EDTA | 0.05 |
| PHASE C: | |
| Almond oil | 3.5 |
| Shark liver oil | 0.5 |
| Squalane | 2.0 |
| Emulsifying wax (pola wax) N.F. | 3.0 |
| Cetyl alcohol | 0.5 |
| BHT | 0.05 |
| BHA | 0.05 |
| Diazolidinyl urea | 1.0 |
| $C_{10}$-$C_{30}$ cholesterol/lanosterol ester | 0.5 |
| Retinyl palmitate $AD_3$ | 0.1 |
| PHASE D: | |
| Collagen amino acids | 0.5 |
| Hydrolyzed animal protein | 0.5 |
| Hydrolyzed elastin | 0.5 |
| Fragrance | 0.5 | wherein, in making said composition, said water is first heated to 75 degrees Celsius and then the additional PHASE A ingredients are mixed in; PHASE B ingredients are added to PHASE A the resulting phase is mixed; PHASE C ingredients are mixed in a separate vessel at 75 degrees Celsius and then mixed into the combined PHASE A AND B. At 40 degrees Celsius, Phase D, which has also been separately mixed, is mixed in to form a stable emulsion.

I have found that the various constituents I have tested are totally capable of being combined together in the concentrations indicated for each to achieve a product with superior cosmetic and therapeutic properties not anticipated from the individual constituents alone. The overall effect may be described as a synergetic effect of the combination of ingredients acting in concert to achieve the overall improved effect on the skin. I have found no prior art to anticipate the superior effect of the formulations I have disclosed herein.

Various modifications of the described invention will occur to those skilled in the art, and it should be understood that the invention includes such modifications as are embraced by, or equivalent to, the invention as claimed herein.

I claim:

1. A cosmetic and moisturizing composition consisting essentially of:

| Ingredient | Weight Percent |
| --- | --- |
| xanthan gum | 0.2–0.5 |
| carbopol | 0–0.02 |
| propylene glycol | 3.0–4.0 |
| triethanolamine (TEA) | 0.02–0.5 |
| tetrasodium EDTA | 0–0.2 |
| squalane | 0.5–30 |
| almond oil | 0–30 |
| sesame oil | 0–30 |
| shark liver oil | 0.5–30 |
| lanolin | 0–3.0 |
| emulsifying wax | 0.5–8.0 |
| polypropylene glycol myristyl ether propionate | 0.5–2.0 |
| glyceryl stearate | 0–5.0 |
| dimethicone | 0–4.0 |
| cetyl alcohol | 0.5–1.0 |
| BHT | 0.05 |
| BHA | 0.05 |
| stearic acid | 0–4.0 |
| diazolidinyl urea | 0.05–1.0 |
| pentaerythritol tetracaprate/caprylate | 0.5–2.0 |
| $C_{10}$-$C_{30}$ cholesterol/lanosterol ester | 0.1–8.0 |
| $C_{12}$-$C_{18}$ alcohol benzoate | 0–1.0 |
| retinyl palmitate: vitamin D3 5:1 | 0–4.0 |
| collagen amino acids | 0–1.0 |
| hydrolyzed animal protein | 0–1.0 |
| hydrolyzed elastin | 0–1.0 |
| reticulin | 0–0.5 |
| water | as required for 100% |

2. A cosmetic and moisturizing composition consisting essentially of:

| Ingredient | Weight Percent |
| --- | --- |
| xanthan gum | 0.2 |
| carbopol | 0.02 |
| propylene glycol | 4.0 |
| triethanolamine (TEA) | 0.5 |
| tetrasodium EDTA | 0.05 |
| squalane | 2.0 |
| sesame oil | 2.0 |
| shark liver oil | 0.5 |
| lanolin | 0.5 |
| emulsifying wax | 2.0 |
| polypropylene glycol myristyl ether propionate | 2.0 |
| glyceryl stearate | 1.0 |
| dimethicone | 0.5 |
| cetyl alcohol | 0.5 |
| BHT | 0.05 |
| pentaerythritol tetracaprate/caprylate | 1.0 |
| BHT | 0.05 |
| BHA | 0.05 |
| stearic acid | 0.5 |
| fragrance | 0.5 |
| diazolidinyl urea | 1.0 |
| water | as required for 100% |

3. A cosmetic and moisturizing composition consisting essentially of:

| Ingredient | Weight Percent |
|---|---|
| xanthan gum | 0.5 |
| carbopol | 0.2 |
| propylene glycol | 3.0 |
| triethanolamine (TEA) | 0.5 |
| tetrasodium EDTA | 0.05 |
| almond oil | 3.5 |
| shark liver oil | 0.5 |
| squalane | 2.0 |
| emulsifying wax | 3.0 |
| cetyl alcohol | 0.5 |
| BHT | 0.05 |
| BHA | 0.05 |
| diazolidinyl urea | 1.0 |
| $C_{10}$-$C_{30}$ cholesterol/lanosterol ester | 0.5 |
| retinyl palmitate: vitamin $D_3$ 5:1 | 0.1 |
| collagen amino acids | 0.5 |
| hydrolyzed animal protein | 0.5 |
| hydrolyzed elastin | 0.5 |
| fragrance | 0–0.5 |
| water | as required for 100% |

* * * * *